United States Patent
Lang et al.

(10) Patent No.: US 8,852,480 B2
(45) Date of Patent: Oct. 7, 2014

(54) METHOD FOR MANUFACTURING HOLLOW STRUCTURE FOR BREATHING MASK

(75) Inventors: Bernd Christoph Lang, Gräfelfing (DE); Achim Biener, Munich (DE); Johann Sebastian Burz, Wielenbach/Wildzhofen (DE); Johannes Nickol, Munich (DE); Adel Nibu, Munich (DE)

(73) Assignee: ResMed R&D Germany GmbH, Martinsried (DE)

( * ) Notice: Subject to any disclaimer, the term of this patent is extended or adjusted under 35 U.S.C. 154(b) by 893 days.

(21) Appl. No.: 12/449,075

(22) PCT Filed: Oct. 31, 2007

(86) PCT No.: PCT/EP2007/009478
§ 371 (c)(1),
(2), (4) Date: Jul. 22, 2009

(87) PCT Pub. No.: WO2008/089799
PCT Pub. Date: Jul. 31, 2008

(65) Prior Publication Data
US 2010/0101581 A1    Apr. 29, 2010

(30) Foreign Application Priority Data
Jan. 22, 2007   (EP) .................... 07100927

(51) Int. Cl.
*B29C 45/14* (2006.01)
*B29C 45/00* (2006.01)
*A62B 18/02* (2006.01)

(52) U.S. Cl.
USPC ............... 264/267; 264/328.1; 128/205.25

(58) Field of Classification Search
None
See application file for complete search history.

(56) References Cited

U.S. PATENT DOCUMENTS

| | | | | |
|---|---|---|---|---|
| 4,062,357 A | * | 12/1977 | Laerdal | 128/206.26 |
| 4,871,502 A | | 10/1989 | LeBisch et al. | |
| 5,121,745 A | * | 6/1992 | Israel | 128/202.28 |
| 5,219,405 A | | 6/1993 | Weiss | |
| 5,647,357 A | * | 7/1997 | Barnett et al. | 128/206.24 |
| 5,660,174 A | | 8/1997 | Jacobelli | |
| 5,895,537 A | * | 4/1999 | Campbell | 156/73.1 |
| 6,494,206 B1 | | 12/2002 | Bergamaschi et al. | |
| 7,357,845 B2 | * | 4/2008 | Cook | 156/242 |

(Continued)

FOREIGN PATENT DOCUMENTS

| | | |
|---|---|---|
| DE | 197 21 279 A1 | 11/1998 |
| DE | 199 54 517 C2 | 6/2001 |

(Continued)

OTHER PUBLICATIONS

Machine Translation of EP 0 602 424 A1, Oct. 10, 2012.*

(Continued)

*Primary Examiner* — Benjamin Schiffman
(74) *Attorney, Agent, or Firm* — Nixon & Vanderhye P.C.

(57) ABSTRACT

A method for producing a filled hollow structure includes producing an open hollow structure of a first material, positioning the open hollow structure on a tool adapted to hold the open hollow structure, filling the open hollow structure with a filler medium, and closing the filled open hollow structure with a second material. A hollow structure may be produced by such method, and a tool may be structured to perform such method.

33 Claims, 13 Drawing Sheets

(56) References Cited

U.S. PATENT DOCUMENTS

| | | | |
|---|---|---|---|
| 2001/0025641 A1* | 10/2001 | Doane et al. | 128/207.15 |
| 2003/0019496 A1* | 1/2003 | Kopacko et al. | 128/206.24 |
| 2004/0149287 A1* | 8/2004 | Namey, Jr. | 128/205.25 |
| 2009/0032024 A1* | 2/2009 | Burz et al. | 128/206.24 |
| 2009/0044806 A1* | 2/2009 | Burz et al. | 128/205.25 |
| 2009/0078267 A1* | 3/2009 | Burz et al. | 128/206.24 |
| 2009/0107504 A1* | 4/2009 | McAuley | 128/205.25 |
| 2009/0139526 A1* | 6/2009 | Melidis et al. | 128/206.26 |
| 2009/0176051 A1* | 7/2009 | Eifler | 428/99 |
| 2010/0006100 A1* | 1/2010 | Eifler et al. | 128/206.24 |
| 2010/0192955 A1* | 8/2010 | Biener et al. | 128/206.24 |
| 2010/0307504 A1* | 12/2010 | Lang et al. | 128/206.21 |

FOREIGN PATENT DOCUMENTS

| | | |
|---|---|---|
| EP | 0289750 | 11/1988 |
| EP | 0602424 | 6/1994 |
| EP | 1099452 | 5/2001 |
| FR | 1 200 522 | 12/1959 |
| GB | 790 677 | 2/1958 |
| GB | 1119176 A * | 8/1976 |
| WO | WO 2006/050559 A1 | 5/2006 |
| WO | WO 2006/074515 | 7/2006 |
| WO | WO 2007/009782 A1 | 1/2007 |
| WO | WO 2007/120355 A2 | 10/2007 |
| WO | WO 2008/080396 A1 | 7/2008 |

OTHER PUBLICATIONS

Rees, Mold Engineering, 2nd Edition, Hanser, 2002, pp. 238-253.*
Search Report issued in related European Appln. 10188943.4 (Jan. 24, 2011).
International Search Report for PCT/EP2007/009478, dated Feb. 25, 2008.
Search Report issued in related European Appln. 11157873.8 (Jun. 22, 2011).
Communication of a Notice of Opposition issued Sep. 24, 2013 in corresponding EP Application No./Patent No. 11157873.8-1710/2345445.

* cited by examiner

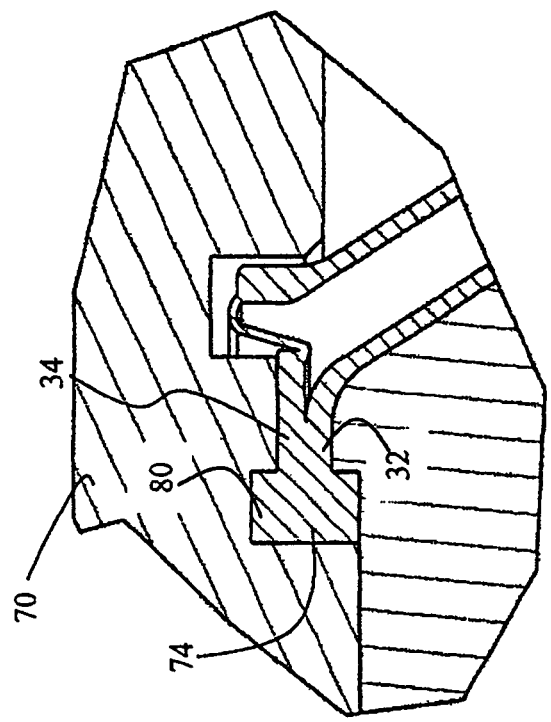
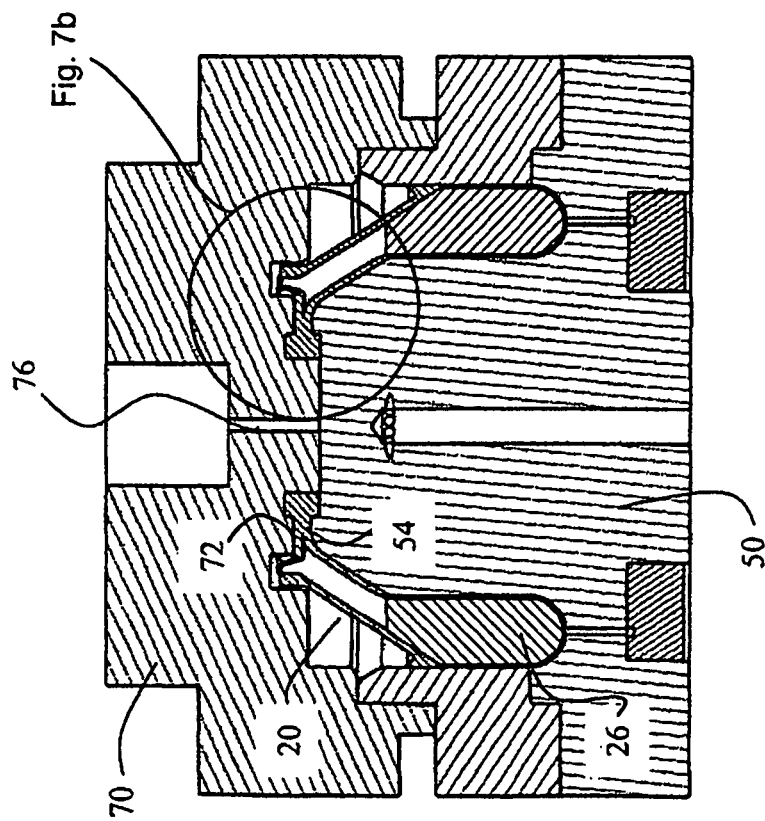
Fig. 7b
Fig. 7a

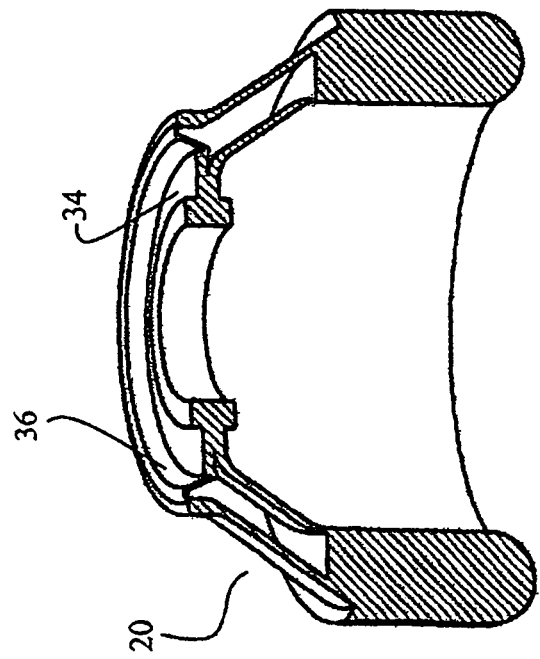
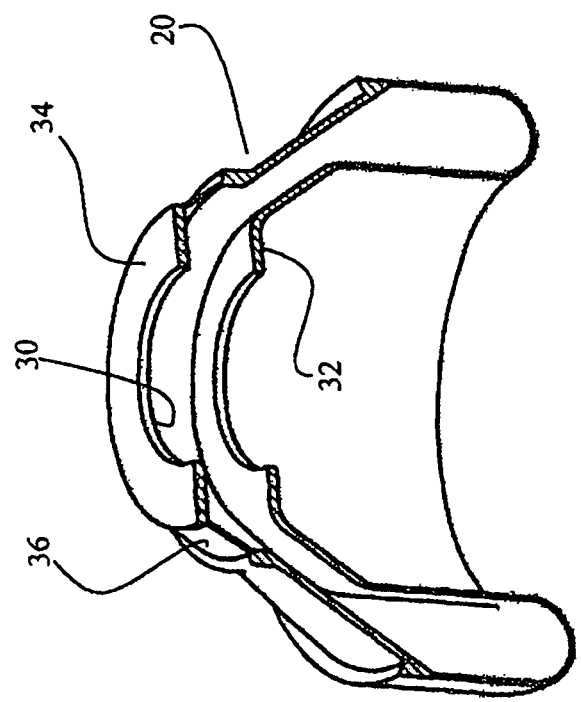
Fig. 11b
Fig. 11a

METHOD FOR MANUFACTURING HOLLOW STRUCTURE FOR BREATHING MASK

CROSS-REFERENCE TO RELATED APPLICATION

This application is the U.S. national phase of International Application No. PCT/EP2007/009478, filed Oct. 31, 2007, which designated the U.S. and claims the benefit of European Patent Application No. EP 07 10 0927.8, filed Jan. 22, 2007, each of which is incorporated herein by reference in its entirety.

FIELD OF THE INVENTION

The invention relates to a method for producing a hollow structure and more particularly to a method for producing a closed and filled hollow structure. Furthermore, the present invention relates to a hollow structure and more particularly to a closed and filled hollow structure obtainable by a method according to the present invention as well as to a tool for producing such hollow structure and/or for performing a respective method.

BACKGROUND OF THE INVENTION

Hollow structures are known in the prior art, for example, in the field of face masks for delivering breathable air to a patient. In such face masks, hollow cushions are used for providing contact zones for contacting the face of the user in order to avoid dents and to improve wearing comfort of the user. Furthermore, such structures are used as a sealing structure for sealing the mask interior from the exterior in the contact region where the mask rests on a user's face.

A disadvantage of hollow structures known in the art is that they are complicated to manufacture and a number of manual manufacturing steps is often necessary. Moreover, such hollow structures are either not closed, i.e., open, or are closed in an ineffective and/or complicated manner.

In particular, it is known to fill a mask cushion with silicone or gel wherein the hollow structure is closed by use of a silicone adhesive.

The solutions known in the prior art are in particular, not easy to handle, not durable, complicated and expensive to manufacture, not suitable for automating, not bio-compatible as well as optically and hygienically objectionable.

SUMMARY OF THE INVENTION

One aspect of the present invention relates to a method for producing or manufacturing a hollow structure and particularly a filled hollow structure which overcomes the deficiencies of the prior art. More particularly, an aspect of the present invention relates to a method for manufacturing the hollow structure which is easy and efficient to carry out, which can be automated, and which provides for a durable as well as an optically and hygienically improved hollow structure. Moreover, an aspect of the present invention relates to a tool for producing a hollow structure as well as an improved hollow structure.

Another aspect of the present invention relates to a method for producing a filled hollow structure comprising producing an open hollow structure of a first material, e.g., a structure having a hollow or hollow area such as a pocket or a cavity wherein at least a portion of the hollow is open towards the outside of the structure, positioning the open hollow structure in or on a tool adapted to hold the open hollow structure, at least partially filling the open hollow structure with a filler medium, and closing the filled open hollow structure with a second material. The filled open hollow structure may be closed by clamping jaws that are adapted to provide a cavity into which the portions of the hollow structure to be closed extend. In this context, it is to be noted that clamping jaws as referred to in the present application are not limited to perform a pivoting motion towards one another but may also or alternatively clamp via a linear motion or the like.

According to the present invention a filler medium is preferably considered to be a medium being non-releasably contained in a structure, i.e. a medium which is to stay in a structure, such as a hollow structure. According to the present invention a filled hollow structure once closed is preferably considered to non-releasably contain the filler medium.

The cavity may be filled with a second material adapted to close (and/or seal) the open hollow structure. In an embodiment, before and/or while filling the cavity with the material for closing and/or sealing the open hollow structure, pressure may be applied to the cavity and/or by the clamping jaws to the opening of the hollow structure in order to securely close and/or seal the hollow structure. This arrangement may prevent the material for closing and/or sealing the open hollow structure from entering the open hollow structure.

According to an embodiment, the sequence of method steps may be changed, e.g., the open hollow structure may be provided with a connection and is first closed and/or sealed, as discussed above, and subsequently at least partially filled with a filler medium through the connection. In an embodiment, the connection may act as a one way valve so that the connection does not need to be closed or sealed after the filling step. Also, the connection may be closed and/or sealed after the filling step. According to a further embodiment, the open hollow structure may be first closed and/or sealed. A vacuum may be applied to the hollow structure and the structure may be filled with a filler medium. The application of vacuum and the filling may be carried out subsequently and/or simultaneously. The application of a vacuum may be advantageous in case, e.g., a viscous gel is used as a filler medium.

In an embodiment, the open hollow structure may be made of a first material and a second material may be used for closing the open hollow structure. One or both of the first and second materials may be an elastic material.

The hollow structure may be made of a flexible first material, e.g., a plastic or synthetic material such as an elastomer material or a material comprising elastomer components. For example, the hollow structure may be made of silicone such as liquid silicone rubber (LSR), or thermoplastic elastomer (TPE). In an embodiment, an open hollow structure may be an injection molded plastic skin, e.g., made of silicone or a liquid silicone rubber (LSR). In an embodiment, the hollow structure may include a first portion to be filled by filler medium, a second portion which is constructed as a connection structure or transition portion between the first portion and a third portion which is adapted for filling and closing or sealing the hollow structure. Alternatively, the second portion may be optional and the hollow structure may comprise only the first and the third portions.

The third section of the hollow structure according to an embodiment, i.e., the area for filling and sealing the hollow structure, may be designed as or include a bi-stable membrane which may assume two positions, e.g., a first position in which the hollow structure is open for filling the structure and a second position in which the hollow structure is closed for closing and/or sealing.

The geometry of the hollow structure in the third section may be circular, oval, non-circular, linear, etc. In an embodiment, the third section may include two opposite flattened areas which are adapted to close the hollow structure when abutting each other.

Furthermore, the hollow structure may include thin or skin-like outer walls which may have, according to embodiments, a differing wall thickness and/or topography. According to an embodiment, the open hollow structure may be described as having a generally tube-like form which has been put over itself resulting in a hollow structure having an inner wall and an outer wall which merge at one end of the structure via a bottom or transition wall and which is open at the other end of the structure. However, it is to be understood that the tube-like basic form as referred to above is not restricted to one diameter or a circular form but may comprise different cross sections, diameters, wall thicknesses, etc. In an embodiment, when used in the field of face masks for delivering breathable air to a patient, the hollow structure may have a generally tubular ring-like form with a generally triangular cross-section, particularly at its bottom or transition wall serving as a contact zone for resting on a patient's face. In an embodiment, when used in the field of face masks for delivering breathable air to a patient, the wall thickness may vary and may lie in the range of about 0.1 mm to about 7 mm. In an embodiment, the hardness of the hollow structure may lie in the range from about 1 to 80 Shore A, e.g., about 20 to 60 Shore A or in the range of about 3 to 10 Shore A or about 5 Shore A or 40 Shore A. The hardness may depend on the spring and damping properties of the material and the ability to be easily demolded.

The filler medium which is filled into the open hollow structure may include a fluid, i.e., a gaseous, dispersible and/or liquid fluid, an expandable fluid, a foam, a powder and/or gel. According to embodiments, a mixture of the above media may be used, e.g., two gels of different hardness or viscosity.

The second material used for closing the open hollow structure may be suitable to seal the opening of the open hollow structure in a liquid and/or gas tight manner. In an embodiment, the fluid may include the same material as that from which the open hollow structure is made. According to an embodiment, the material for closing the open hollow structure may be silicone or liquid silicone rubber. According to an embodiment, the second material used for closing the filled hollow structure is not a silicone glue or is not a silicone adhesive.

The method according to an embodiment of the present invention may further include curing the material for closing the open hollow structure. Such curing may involve, depending on the conditions and the materials used, e.g., the addition or removal of energy, application of temperature, i.e., heat or cold, radiation, e.g., UV-light, the addition of further substances and/or time factors, i.e., waiting time, etc., foaming, and/or initiation of crystallization. During curing, the form or geometry of the closed or sealing area may be controlled, e.g., by the clamping jaws and the respective cavity.

In an embodiment, the open hollow structure may be held on the tool for holding the open hollow structure by the provision of a firm fit by the application of compressed air and/or vacuum. Also, the closed hollow structure may be removed from the tool by the use of compressed air and/or vacuum.

In an additional step, a vacuum may be applied to the hollow before the filler medium is inserted into the hollow. The application of the vacuum to the hollow sucks air out of the hollow before the filler medium is inserted into the hollow so that an improved, e.g., void free, filling of the hollow may be achieved.

In a further additional step, a vacuum may be applied to the hollow and the filler medium after the open hollow structure has been filled with the filler medium. This step may improve the optical and hygienically appearance of the filled hollow structure as well as its mechanical properties by reducing or eliminating voids occurring in the filler medium and by providing a desired shape or structure to the hollow structure.

The material for closing the open hollow structure may be, according to an embodiment, applied into the cavity provided by the clamping jaws under pressure. Further, the clamping jaws may be heated for curing the material for closing the open hollow structure.

According to an embodiment, the method according to an embodiment of the invention may further include coating the hollow structure and/or the filler medium in the hollow, particularly in order to improve durability and/or optical and/or hygienically properties. According to a further embodiment, the coating step may be performed after applying a vacuum to the hollow and the filler medium, e.g., in order to provide a desired shape, and eliminate voids in the filler medium, etc.

According to an embodiment, the hollow structure may include a connection structure adapted to connect the hollow structure to further structures. For example, according to an embodiment, the hollow structure may form part of a face mask and thus may be suitable to be connected with other structures, to fulfill other or additional functions, and/or to additionally form other structures in order to form such a mask.

According to a further embodiment, the hollow structure may include a connection adapted to allow a vacuum to be applied to the hollow. The connection allows the vacuum to shape the structure and to fix the respective shape. In an embodiment, the connection may be closed so that the vacuum may be maintained inside the hollow structure.

The filler medium may be suitable to store heat and/or cold. According to a further embodiment, the filler medium may be structure to harden and/or soften if certain predetermined conditions are met. In an embodiment, the filler medium may harden and/or soften upon a trigger signal, such as a signalization signal, or upon the application of heat or cold, etc.

Another aspect of the present invention relates to a hollow structure produced by a method according to an embodiment of the present invention as well as a tool for producing such hollow structure and/or for performing a method according to an embodiment of the present invention Another aspect of the invention relates to a hollow structure including an inner wall, an outer wall spaced from the inner wall to define a hollow between the inner and outer walls, a bottom wall that couples the inner and outer walls, and first and second portions that define a closable opening into the hollow. The first portion is coupled to the outer wall by a membrane that allows the first portion to move between (1) a first, opened position in which the first portion is spaced from the second portion to allow access to the hollow through the opening, and (2) a second, closed position in which the first portion abuts the second portion to close the opening.

Another aspect of the invention relates to a tool for producing a hollow structure. The tool includes a rotatable table providing a plurality of working positions and one or more fixed working stations each adapted to perform one or more manufacturing operations. Each working position includes a working tool adapted to hold a respective hollow structure in an operative position. The table is adapted to be rotated so that each working position may pass by the one or more fixed working stations for performance of one or more manufacturing operations on the respective hollow structure.

According to an embodiment, the hollow structure may constitute a cushion to be used in face masks, e.g., breathing masks, in order to provide a tight and comfortable contact between mask and a user.

Other aspects, features, and advantages of this invention will become apparent from the following detailed description when taken in conjunction with the accompanying drawings, which are a part of this disclosure and which illustrate, by way of example, principles of the invention.

BRIEF DESCRIPTION OF THE DRAWINGS

The accompanying drawings facilitate an understanding of the various embodiments of this invention. In such drawings:

FIG. 6b is an enlarged view of a portion of FIG. 6a;

FIG. 7a is a cross-sectional view of a second step of the closing step showing the tool, hollow structure and clamping means wherein the cavity is filled with a material for closing the open hollow structure according to an embodiment of the present invention;

FIG. 7b is an enlarged view of a portion of FIG. 7a;

FIG. 11a is a cross-sectional view of a hollow structure wherein the closing area is designed as a bi-stable membrane according to an embodiment of the present invention, the bi-stable membrane in an open position;

FIG. 11b is a cross-sectional view of the hollow structure shown in FIG. 11a showing the bi-stable membrane in a closed and sealed position.

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, each single feature or combination of features in any of the embodiments may constitute an additional embodiment.

In this specification, the word "comprising" is to be understood in its "open" sense, that is, in the sense of "including", and thus not limited to its "closed" sense, that is the sense of "consisting of". A corresponding meaning is to be attributed to the corresponding words "comprise", "comprised" and "comprises" where they appear.

Figure 1:
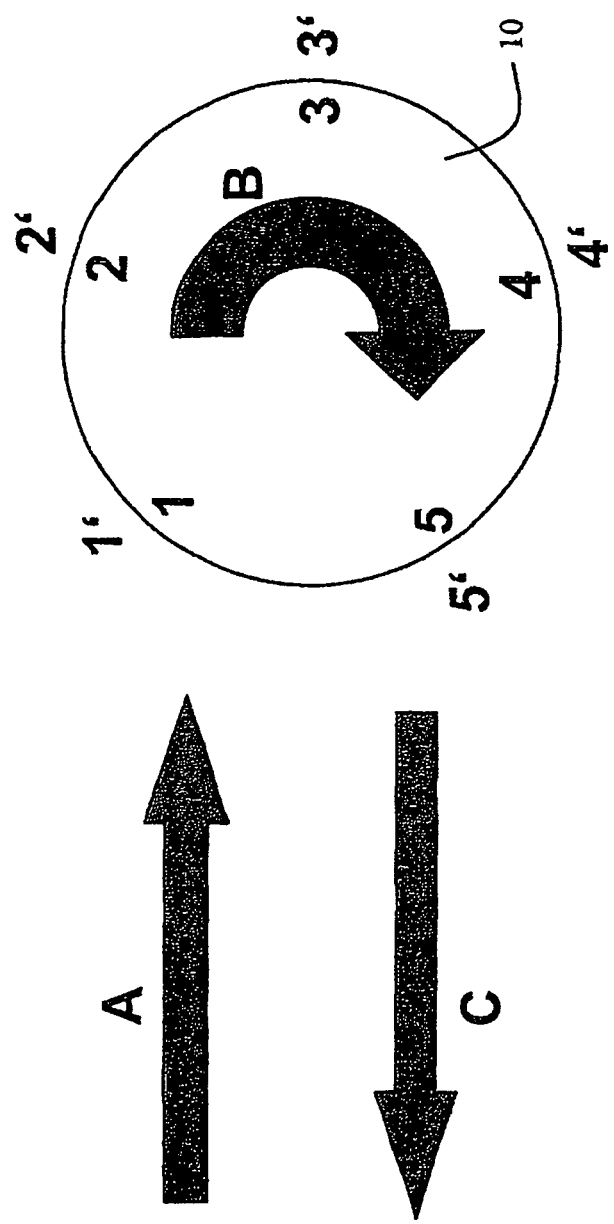
FIG. 1 is a schematic view of a production line according to an embodiment of a method of the present invention.

FIG. 1 is a schematic view of a method for producing a filled hollow structure according to an embodiment of the present invention. In particular, arrows A, B and C show the way or path of the product according to steps of the method according to an embodiment of the present invention.

Arrow A indicates the feeding of an open hollow structure to a tool for producing a filled hollow structure, Arrow B indicates the path or successive and/or simultaneous steps of the hollow structure along the tool for producing a filled hollow structure, and Arrow C illustrates the removal of the filled hollow structure from the tool. The open hollow structure may be constructed of an injection molded plastic structure having thin wall thicknesses, e.g., made of silicone (e.g., liquid silicone rubber). The open hollow structure is inserted from the direction as indicated by arrow A and positioned on a tool for holding the open hollow structure in working position 1. In the illustrated embodiment, working position 1 may be located on a turntable 10 so that the open hollow structure may be successively carried along positions 1 to 5 on table 10. At each position 1 to 5, one or more method steps may be carried out according to embodiments of the present invention.

Figure 2:
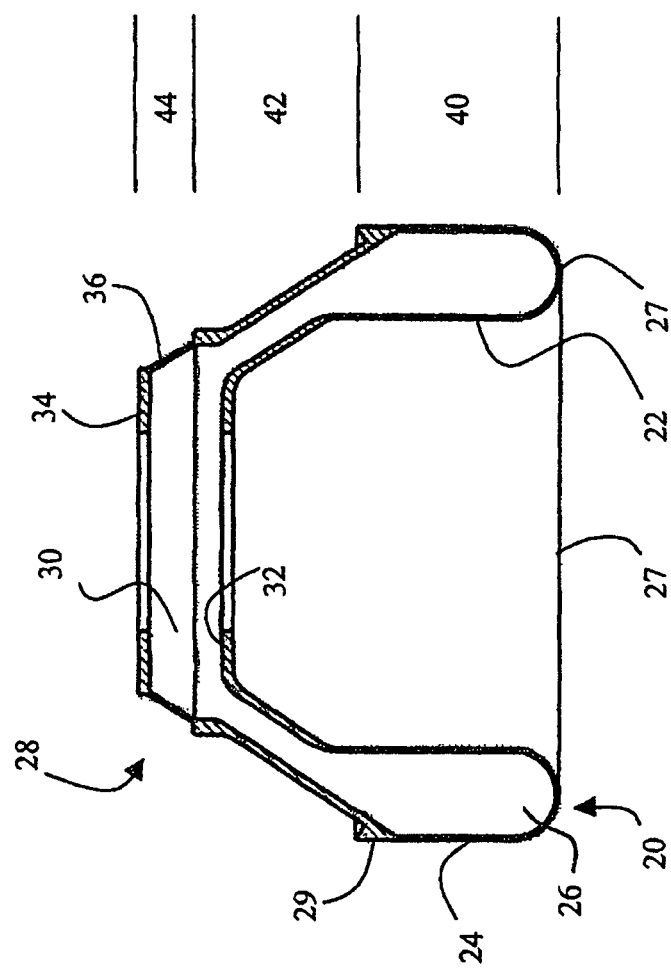
FIG. 2 is a cross-sectional view of an open hollow structure according to an embodiment of the present invention.

FIG. 2 illustrates an embodiment of an open hollow structure adapted to be inserted into the tool at position 1. As illustrated, open hollow structure 20 includes a thin inner wall 22 and a thin outer wall 24 wherein a hollow or hollow area 26, such as a pocket or a cavity, is formed between inner wall 22 and outer wall 24. Inner wall 22 and outer wall 24 merge at one end of the structure via a bottom or transition wall 27. Hollow structure 20 has a basically ring shaped form when viewed from the bottom in FIG. 2. Hollow structure 20 also includes a filling or sealing area 28 that defines an opening 30 in which the hollow area 26 is open to the environment. In the illustrated embodiment, opening 30 is a circular slot extending between a first closing area 32 and a second closing area 34. Closing areas 32 and 34 may be designed as flattened, basically ring-shaped portions of the hollow structure which are able to close the open hollow structure, e.g., when abutting each other in mutual contact. As illustrated, closing area 32 forms part of or is directly or indirectly connected to inner wall 22 whereas closing area 34 forms part of or is directly or indirectly connected to outer wall 24. As shown in FIG. 2, closing or sealing area 28 and hollow structure 20 have a substantially circular form. However, the hollow structure and/or the closing area of the hollow structure is not limited to circular or substantially circular shapes, but may have other suitable forms and shapes as will be discussed below in further detail. According to an embodiment, the hollow structure and/or the closing area of the hollow structure may have the form and/or configuration of face masks for delivering breathable air to a patient and/or of hollow cushions of such masks, e.g., a basically triangular form.

Figure 3:
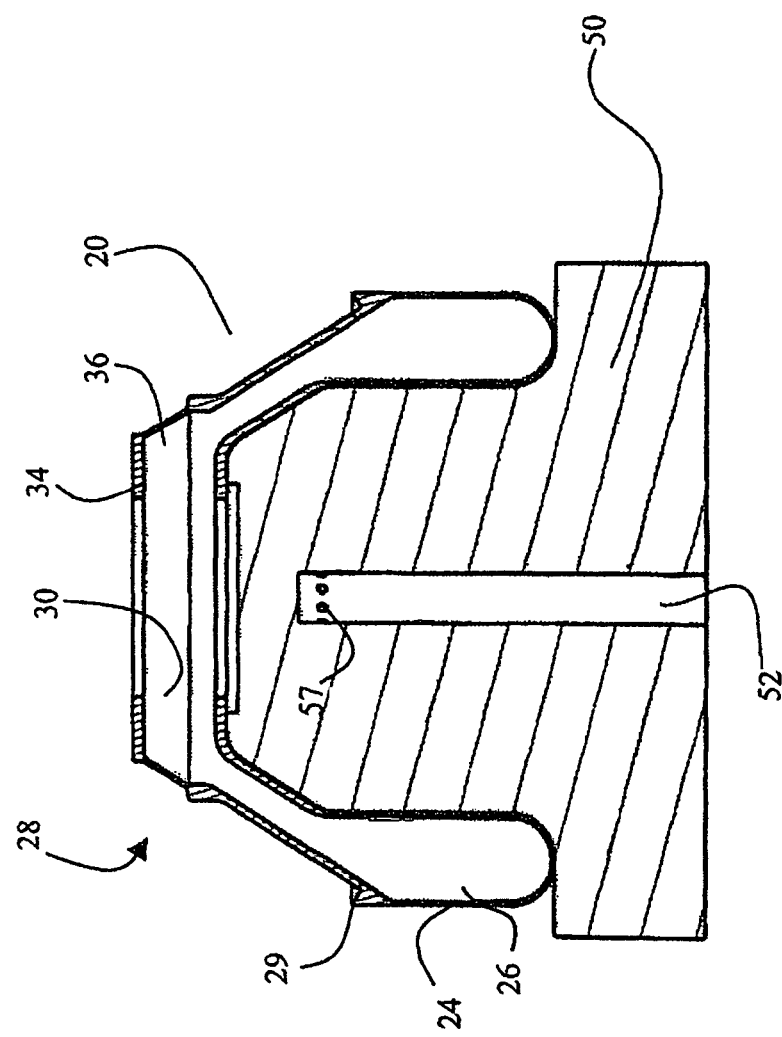
FIG. 3 is a cross-sectional view of an open hollow structure placed on a tool for holding the open hollow structure according to an embodiment of the present invention.

FIG. 3 shows the open hollow structure 20 at position 1 (FIG. 1) in which the open hollow structure 20 is placed on a tool 50 for holding the open hollow structure 20. In the illustrated embodiment, the geometry of tool 50 substantially conforms to the geometry of the hollow structure 20 and particularly to the geometry of inner wall 22. As illustrated, tool 50 comprises a duct 52 and nozzles or channels 57 adapted to apply a vacuum and/or compressed air for use in holding hollow structure 20 on the tool 50 and/or releasing or removing hollow structure 20 from the tool 50.

Figure 4:
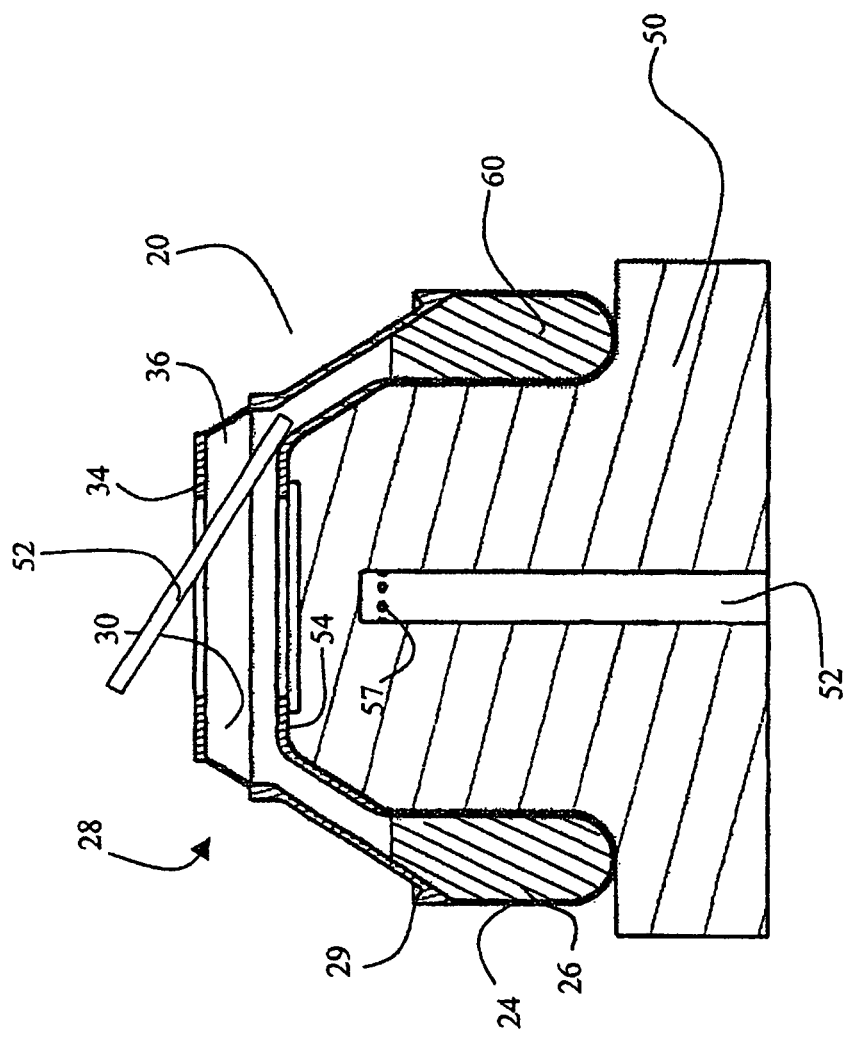
FIG. 4 is a cross-sectional view of an open hollow structure placed on a tool for holding the open hollow structure when the filler medium is filled into the open hollow structure according to an embodiment of the present invention.

FIG. 4 illustrates the hollow structure 20 at working position 2 (FIG. 1) in which the open hollow structure 20 is filled with a filler medium 60, e.g., via injection pin 52. In the illustrated embodiment, injection pin 52 is adapted to be connected to a supply of filler medium and is adapted to be inserted into the opening 30 of the hollow structure 20 to provide fluid communication between the supply of filler medium and the hollow area 26 of hollow structure 20. According to an embodiment, more than one injection pin 52 may be used for filling hollow structure 20.

Figure 5:
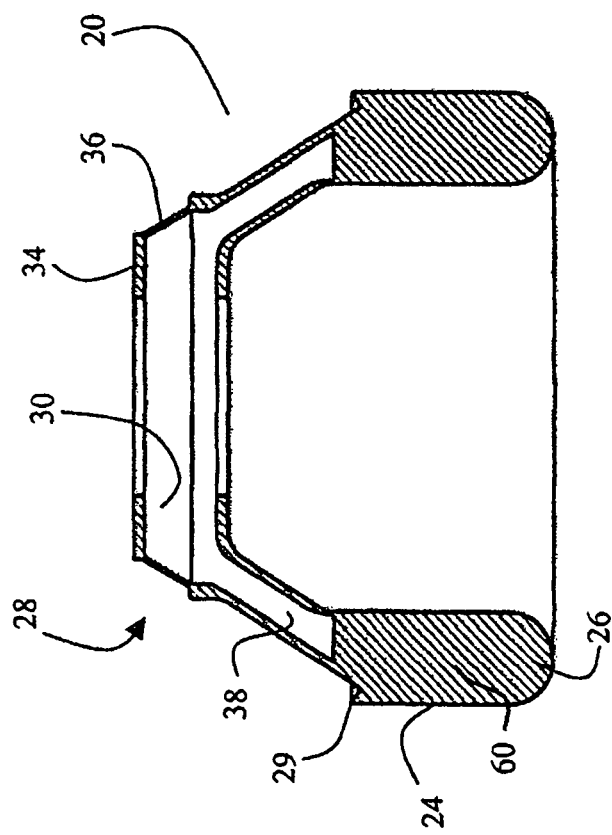
FIG. 5 is a cross-sectional view of a filled open hollow structure according to an embodiment of the present invention.

FIG. 5 shows the hollow structure 20 filled with a filler medium 60 and isolated from the tool 50. As illustrated hollow area 26 is completely filled with filler medium 60 and a remaining cavity or hollow area 38 (provided in an intermediate second section 42 (see FIG. 2) of hollow structure 20 reaching to the closing area 28) is not filled with filler medium 60. In alternative embodiments, hollow area 26 may be only partially filled with filler medium 60 or the cavity or hollow area 38 of the intermediate second section of hollow structure 20 may be fully filled with filler medium 60.

In an embodiment, e.g., when the filler medium is a gel or a silicone gel, the gel may be inserted cold or at room temperature as a liquid and may be subsequently heated to cure, as discussed further below. According to a further embodiment, the gel may be inserted into the hollow area 26 preheated. This arrangement allows a faster cure. According to another embodiment, the gel may be inserted pre-cooled into the hollow area 26. This arrangement slows down the curing process, e.g., if the gel is curing too fast.

As a further step, preceding the filling of the hollow area 26 with a filler medium 60, a vacuum may be supplied to the hollow area 26 in order to suck air out of the hollow area 26 before the filler medium, such as a gel, is inserted.

Furthermore, the gel may be allowed to only cure partially to achieve desired properties of the structure.

Figure 6B:
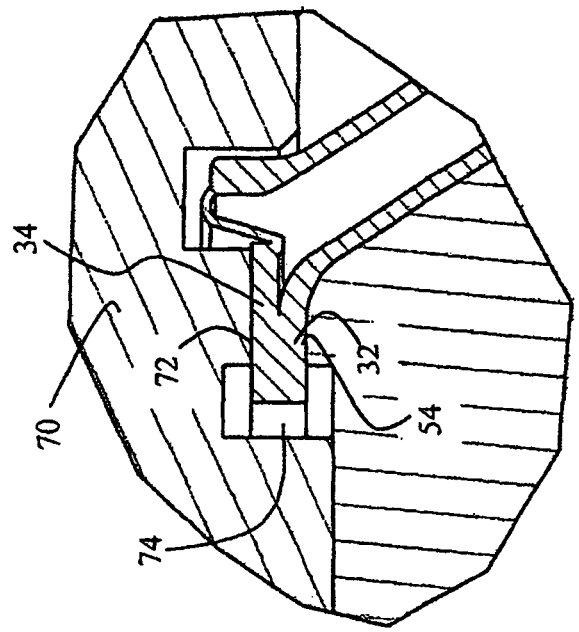
Figure 6A:
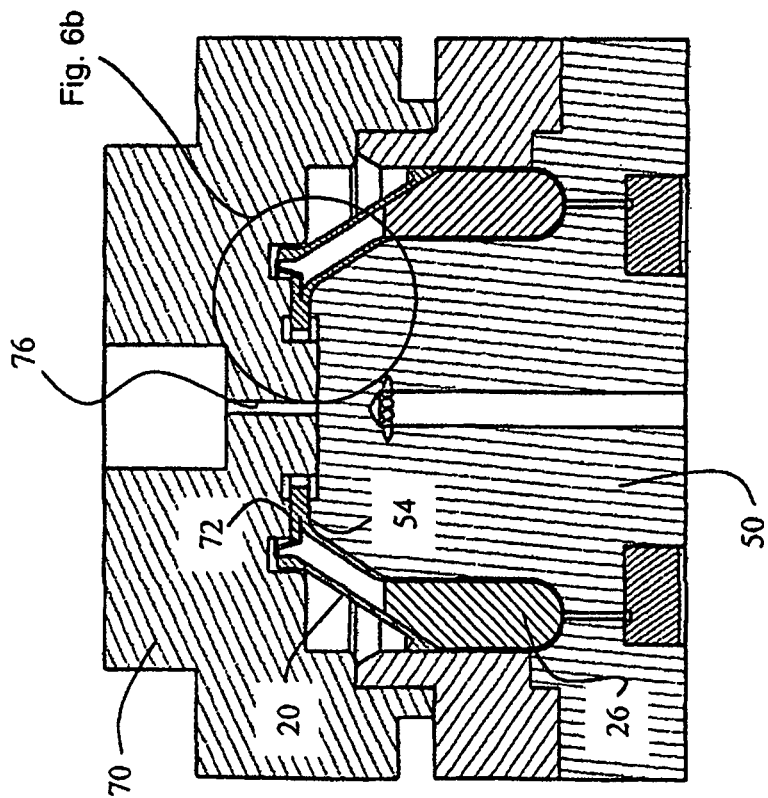
FIG. 6a is a cross-sectional view of the closing or sealing area of an open hollow structure clamped by clamping means providing a cavity according to an embodiment of the present invention.

FIGS. 6a and 6b illustrate the hollow structure at working position 3 (FIG. 1). FIG. 6a shows hollow structure 20 filled with a filler medium 60 and placed on tool 50 wherein a second tool 70 is provided for closing the filled open hollow structure. In particular, tools 50 and 70 are configured to cooperate in a manner so as to close the filled open hollow structure 20. In an embodiment, hollow structure 20 and tool 50 are configured such that a third section 44 (see FIG. 2) of hollow structure 20, i.e., the filling and the closing section 28, is located on a closing surface 54 of tool 50. Tool 70 includes a corresponding closing surface 72 which is adapted to cooperate with tool 50 and particularly with closing surface 54 of tool 50 so as to allow closing of the filled open hollow structure. In an embodiment, closing surfaces 54 and 72 are configured so that when tool 70 is positioned relative to tool 50, the tool 70 urges closing area 34 of hollow structure 20 towards closing area 32 so that the closing areas 32 and 34 mutually abut each other and take a closed position as shown in FIGS. 6a-6b. Moreover, tools 50 and 70 and particularly closing surfaces 54 and 72, respectively, provide a cavity 74 in the area of abutting closing surfaces 32 and 34 of hollow structure 20. As best shown in FIG. 6b, —cavity 74 surrounds an end portion of closing areas 32 and 34 and thus of hollow structure 20. Particularly, cavity 74 is provided such that it surrounds the opening 30 (now a closed opening 30) of hollow structure 20.

As shown in FIG. 6a, tool 70 includes a channel system 76 which is in fluid communication with cavity 74 and is adapted to provide a material for closing the open hollow structure to cavity 74. In an embodiment, channel system 76 allows a material for closing the hollow structure 20 to be filled into cavity 74, e.g., under pressure. According to an alternative embodiment, channel system 76 may be additionally or solely provided in tool 50.

Figure 7C:
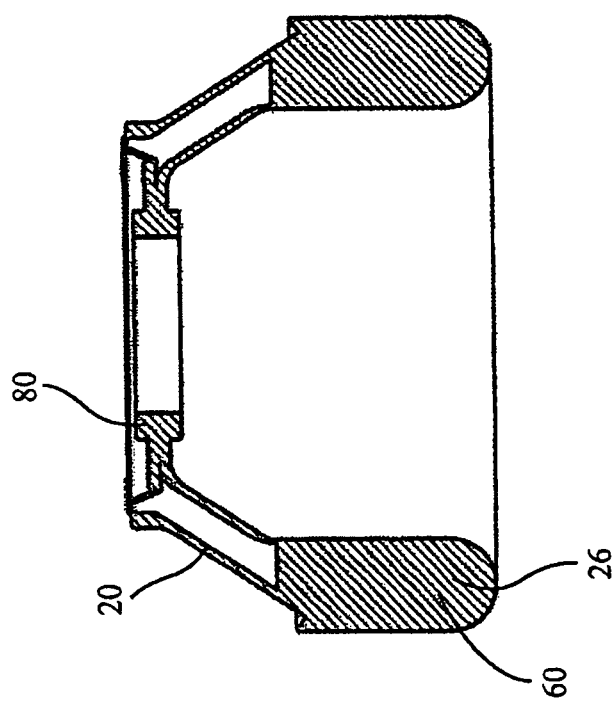
FIG. 7c is an isolated view of a filled and closed hollow structure according to an embodiment of the present invention.

FIG. 6b shows an enlarged view of the area around the cavity 74 and the closing areas 32 and 34 of hollow structure 20. FIGS. 7a and 7b show cavity 74 being filled with a material 80 for closing the hollow structure 20 in the area of opening 30 and/or closing areas 32 and 34. FIG. 7c shows the hollow structure 20 without tools 50 and 70, e.g. after completion of filling and closing of the hollow structure.

According to an embodiment, tool 50 and/or tool 70 may be adapted to assist curing of the material for closing the open hollow structure. For example, tools 50 and/or 70 may be heatable and/or coolable to allow the material 80 filled into cavity 74 to cure.

Figure 8:
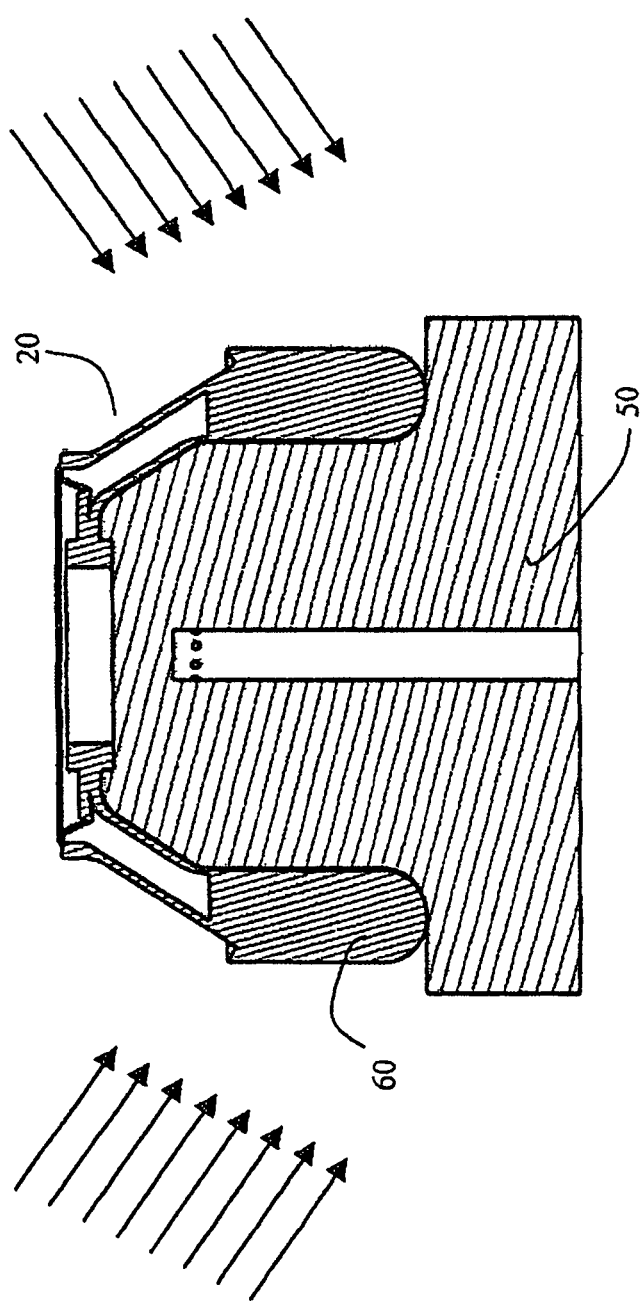
FIG. 8 is a cross-sectional view of a curing step according to an embodiment of the present invention.

FIG. 8 illustrates the hollow structure 20 at working position 4 (FIG. 1) wherein the filler medium 60 inside the closed and filled hollow structure 20 may be cured. Such curing may be achieved by, e.g., the application of temperature, radiation, etc. In a embodiment, tool 50 may be heatable to assist curing of filler medium 60.

Figure 9:
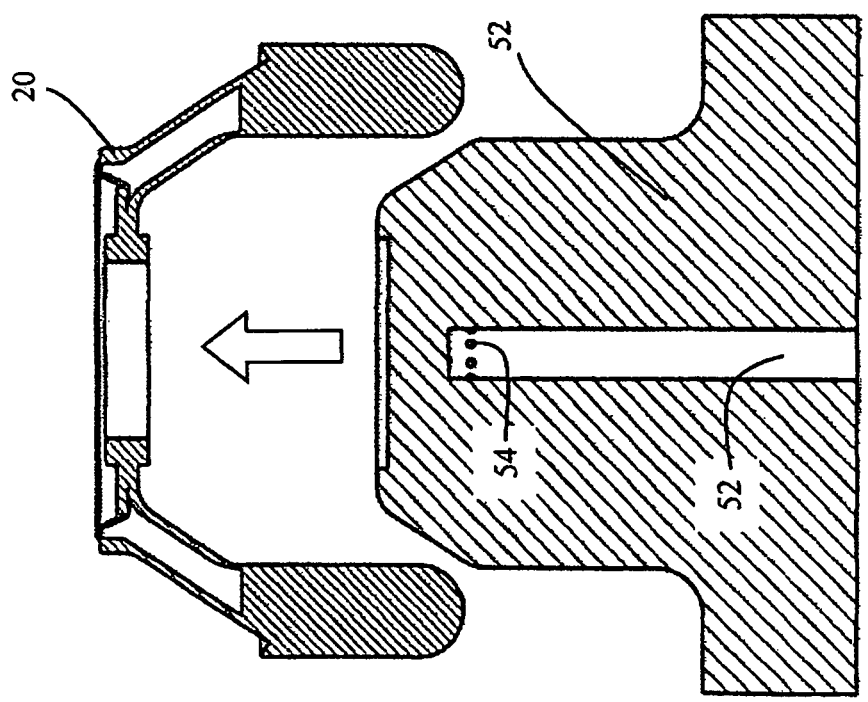
FIG. 9 is a cross-sectional view of the closed hollow structure being removed from the tool after completion of the method according to an embodiment of the present invention.

FIG. 9 shows the hollow structure 20 at working position 5 (FIG. 1) in which the hollow structure 20 is removed from tool 50, e.g., by applying pressured air through duct 52 and nozzles 54 and/or by releasing the vacuum applied to hold hollow structure 20 on the tool 50 (e.g., following filling, closing, and curing of the hollow structure). The sequence/order of filling, closing, curing, and removing may be changed or simultaneous.

Figure 10:
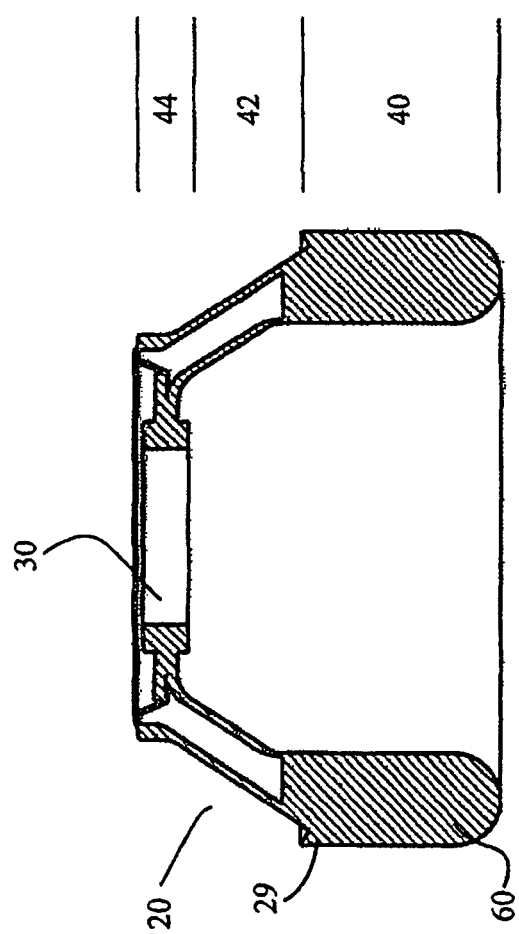
FIG. 10 is a cross-sectional view of a filled hollow structure according to an embodiment of the present invention.

FIG. 10 shows a hollow structure 20 after having been filled with filler medium 60 and after having been closed in the area of opening 30 in the manner as described above. As illustrated, hollow structure 20 includes three sections 40, 42, 44. First section 40 comprises cavity 26 filled or to be filled with filler medium 60, third section 44 comprises opening 30 and closing areas 32 and 34, and second section 42 is arranged between first section 40 and third section 44 and constitutes a transition between first section 40 and third section 44. According to an embodiment, section 42 constitutes or comprises a connection structure 29 (also see FIGS. 2-5) suitable for connecting hollow structure to a superior structure, such as a face mask or a part of a face mask. Alternatively, hollow structure 20 may comprise further means or structure for allowing or facilitating a connection of hollow structure 20 to further structures and to allow an assembly of hollow structure 20 together with further means and structures to become a final product, such as a face mask.

As shown in FIG. 10, hollow structure 20 may comprise different wall thicknesses as well as various changes in geometry depending on the individual requirements of the desired use.

FIG. 11a shows the hollow structure in an unfilled and open state and FIG. 11b shows the hollow structure in a filled and closed or sealed state. As discussed above, hollow structure 20 comprises a closable opening 30, e.g., arranged between areas 32 and 34. Areas 32 and 34 may be constructed as comprising mutual surfaces which when abutting each other allow the opening 30 of hollow structure 20 to be sealingly closed as discussed above with reference to FIGS. 6 and 7. As shown in FIGS. 2-5 and 11a-11b, hollow structure 20 includes a bi-stable membrane 36, e.g., in the area of area 34. Bi-stable membrane 36 allows section 34 to assume two stable positions. In this context, the term "stable" refers to positions in which section 34 remains without application of additional external forces. When section 34 or bi-stable membrane 36 are in a first, opened position (as shown in FIG. 11a), hollow structure 20 is open and a filler medium 60 may be injected. In a second, closed position, as shown in FIG. 11b, section 34 abuts section 32 so that opening 30 and thus hollow structure 20 are closed. In an embodiment, membrane 36 may be structured so that section 34 may maintain either the first or second stable position, e.g., even if section 34 is slightly moved from the stable position it will tend to return to the respective stable position. In an exemplary embodiment, only if section 34 travels a defined way from a stable position towards the other stable position, it will spring or snap to the other stable position after having been moved over a point of no return. These effects may be achieved by the provision of bi-stable membrane 36 which is designed accordingly by varying its geometry and wall thickness depending on the overall geometry of opening 30, area 32 and particularly area 34.

At working position 5 as indicated in FIG. 1, the filled, enclosed hollow structure 20 may be removed from the table 10, see arrow C. Subsequently, further method steps may be applied.

Figure 12:
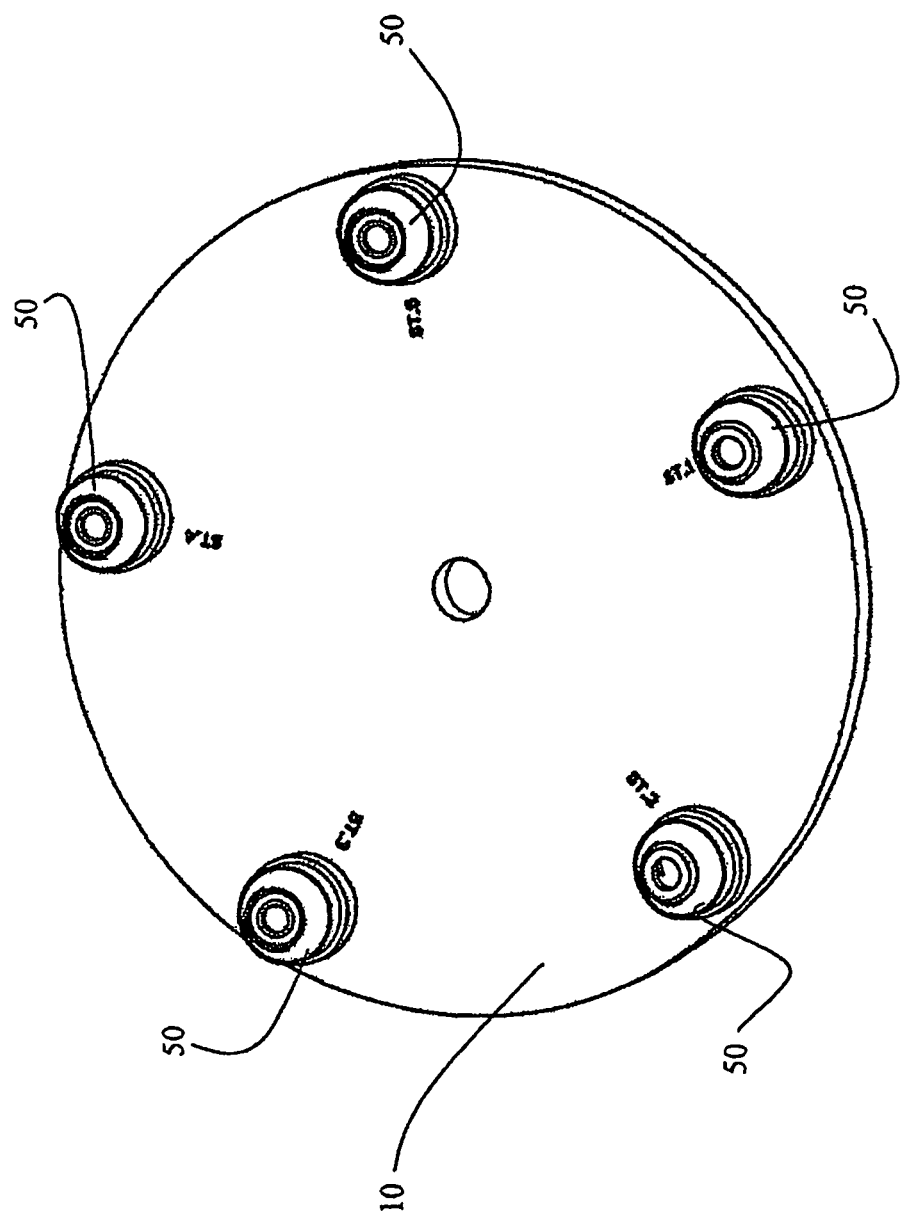
FIG. 12 is a perspective view of an automated production line according to an embodiment of the invention.

FIG. 12 shows a schematic three-dimensional view of a table 10 with five working positions at which tools 50 are provided. A hollow structure 20 positioned on a tool 50 at working position 1 may thus undergo the respective method treatments as discussed above by turning table 10 in the direction of arrow B as indicated in FIG. 1 so that the respective hollow structure 20 moves from a first working position to a second working position, etc. Further means for carrying out the respective method steps are provided at working stations 1', 2', 3', 4', 5' outside the table 10 and apply the same method steps to different hollow structures 20 passing the working station after each cycle. Accordingly, referring to FIG. 1, a hollow structure is placed on tool 50 at working position 1 adjacent working station 1', and then the hollow structure is moved by turning turntable 10 to move working position 1 to working station 2'. At the same time, working position 5 moves to working station 1' and a new hollow structure is placed onto respective tool 50 at working position 5. At working station 2', filling of the filler material is carried out. In the next cycle, the hollow structure at working position 1 moves from working station 2' to working station 3' where the closing of the hollow structure is performed as discussed above. At the same time, hollow structure 20 positioned on working position 5 moves from working station 1' to working station 2'. After further method steps have been performed, i.e., curing at working station 4' and removing the finished hollow structure at working station 5', working position 1 again arrives at working station 1' and a new hollow structure may be inserted. It is to be noted, as discussed above, that step 4 regarding curing of the inserted filler material may be an optional step of the method according an embodiment of the present invention.

It should be appreciated that the above description as well as the figures relate to an exemplary embodiment of a method and product according to an embodiment of the present invention. However, the respective method as well as the product and tool and in particular their geometry should not be considered as being restricted by the above example. According to further embodiments, a hollow structure, may not have a circular cross section in top and/or bottom views but may comprise different forms. For example, a hollow structure may have a substantially triangular form when viewed from the top and/or bottom. However, the hollow structure may also comprise further symmetrical and non-symmetrical forms in top and/or bottom views such as a rectangular, elliptical, round, ring-shaped and/or linear, etc.

As discussed above, the filler medium may be a fluid such as a gaseous and/or liquid medium, a gel, a powder, beats or pellets, a foam or a foamable medium, etc. In an embodiment, the filler medium may be structured to allow the hollow structure to yield or react resiliently upon application of external pressure and provide a soft and comfortable deformable appearance. The softness or hardness of the filler medium or the filled hollow structure may be adapted according to the requirements of the desired use either during production of the filled hollow structure or after production and prior to use. This may be established by either adjusting the geometry and wall thicknesses of the hollow structure to adjust the general support of the filler medium, adjusting the degree up to which the hollow area is filled with the filler medium, adjusting the filler medium itself, as well as a combination of these factors. For example, the hollow structure may comprise different wall thicknesses and/or structures for fulfilling additional objects and/or the like.

In an embodiment, the hollow structure comprises a connection that allows a vacuum to be applied to the hollow area, thereby allowing the vacuum to deform the hollow structure so that a desired shape may be achieved and maintaining the vacuum in the hollow area after closure of the respective connection so that the shape of the hollow structure may be maintained. Further, a desired shape or individual shape may be formed and fixed by, e.g., a curing process of the filler medium. In an embodiment, the filler medium and thus the filled hollow structure may still be deformable and soft to a certain degree even after fixation of a desired shape as discussed above. For example, the hollow structure as well as the filling may be at least partially flexible and/or may be brought into a flexible condition.

In an embodiment, the hollow structure may be made of a silicone material, e.g., liquid silicone rubber, and the filler medium may also be made of a silicone material, e.g., liquid silicone rubber, in a substantially liquid aggregate state (e.g., such as gel) which may be achieved by partial curing or adding additives.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A method for producing a filled hollow structure of a breathing mask, comprising:
producing an injection-molded open hollow structure of a first material;

positioning the open hollow structure on a tool adapted to hold the open hollow structure;

filling the open hollow structure with a filler medium while the hollow structure is positioned on the tool;

closing the filled open hollow structure with a second material while the hollow structure is positioned on the tool; and curing the second material when the second material is in a different state than the first material, wherein the second material is an elastomer, and wherein an end portion of the hollow structure forms a contact zone configured to rest against a patient's face.

2. A method according to claim 1, wherein the first material is silicone.

3. A method according to claim 1, wherein the second material is silicone, liquid silicone rubber (LSR), or thermoplastic elastomer (TPE).

4. A method according to claim 1, wherein the second material comprises silicone, liquid silicone rubber (LSR), thermoplastic elastomer (TPE), and/or the first material.

5. A method according to claim 1, wherein the filler medium is a fluid, gas, liquid, foam, expandable fluid, powder and/or gel.

6. A method according to claim 1, further comprising at least partially curing the filler medium.

7. A method according to claim 1, further comprising removing the hollow structure from the tool.

8. A method according to claim 7, wherein the hollow structure is removed from the tool using compressed air.

9. A method according to claim 1, wherein the open hollow structure is held on the tool by application of compressed air and/or vacuum.

10. A method according to claim 1, wherein the second material is filled into the cavity under pressure or vacuum.

11. A method according to claim 1, further comprising closing the filled open hollow structure by clamping jaws that are adapted to provide a cavity, and filling the cavity with the second material adapted to close the open hollow structure.

12. A method according to claim 11, wherein the jaws are heated or cooled for curing the second material.

13. A method according to claim 1, further comprising providing the hollow structure with further structures to form a breathing mask.

14. A method according to claim 1, wherein the hollow structure is completely or partially filled with the filler medium.

15. A method according to claim 1, wherein the hollow structure is provided with a connection structure adapted to connect the hollow structure to a further structure.

16. A method according to claim 1, wherein the hollow structure comprises a connection adapted to allow a vacuum or pressure to be applied to the hollow structure.

17. A method according to claim 1, wherein the filler medium stores heat and/or cold.

18. A method according to claim 1, wherein the filler medium is adapted to harden and/or soften upon a trigger signal.

19. A method according to claim 18, wherein the trigger signal is a crystallization signal or an application of heat or cold.

20. A method according to claim 1, wherein the hollow body includes a bi-stable membrane.

21. A method according to claim 1, wherein the hollow structure is a cushion for a breathing mask.

22. The method according to claim 1, wherein the step of producing an open hollow structure occurs before the step of positioning the open hollow structure.

23. The method according to claim 1, wherein the step of filling the hollow structure includes filling the hollow structure such that a first area of the hollow structure is filled with the filler material and a second area of the hollow structure is not filled with the filler material.

24. The method according to claim 1, wherein the end portion is configured to seal against the patient's face.

25. A method according to claim 1, wherein the second material is not a silicone glue or a silicone adhesive.

26. A method according to claim 1, wherein the hollow structure includes a first section, a second section and a third section, and wherein the first section has a first hollow area which is filled with the filler medium, the third section has an opening which is closed by the second material, and the second section is arranged between the first section and the third section and includes a second hollow area.

27. A method according to claim 26, wherein the second hollow area is filled with the filler medium.

28. A method according to claim 26, wherein the second hollow area is not filled with the filler medium.

29. A method according to claim 1, wherein the hollow structure has an inner wall and an outer wall, each of the inner wall and the outer wall includes a respective closing area, wherein said closing step includes abutting in mutual contact the respective closing areas and subsequently providing the second material into a cavity that surrounds an end portion of the abutted closing areas.

30. A method for producing a filled hollow structure of a breathing mask, comprising:

producing an open hollow structure of a first material;

positioning the open hollow structure on a tool adapted to hold the open hollow structure;

filling the open hollow structure with a filler medium through at least one opening; and closing the opening, wherein the hollow structure includes a bi-stable membrane that is movable between a first position in which the opening is open and a second position in which the opening is closed.

31. The method according to claim 30, wherein the bi-stable membrane, in the second position, causes a portion of the hollow structure to collapse to close the opening.

32. The method according to claim 30, wherein an end portion of the hollow structure forms a contact zone configured to rest against a patient's face.

33. The method according to claim 32, wherein the end portion is configured to seal against the patient's face.

* * * * *